United States Patent [19]
Chu

[11] Patent Number: 5,626,735
[45] Date of Patent: May 6, 1997

[54] ELECTROPHORESIS SLAB GEL ENCLOSURE FOR GRADIENT GELS

[75] Inventor: Daniel Y. Chu, San Francisco, Calif.

[73] Assignee: Bio-Rad Laboratories, Inc., Hercules, Calif.

[21] Appl. No.: 249,566

[22] Filed: May 26, 1994

[51] Int. Cl.[6] ................................................ C25B 9/00
[52] U.S. Cl. ........................... 204/606; 204/616; 204/618; 204/619
[58] Field of Search ................... 204/182.8, 299 R, 204/606, 616, 618, 619

[56] References Cited

U.S. PATENT DOCUMENTS

| | | | |
|---|---|---|---|
| D. 269,123 | 5/1983 | Hoefer | D24/1.1 |
| 3,980,540 | 9/1976 | Hoefer | 204/180 G |
| 4,169,036 | 9/1979 | Anderson et al. | 204/299 R |
| 4,518,476 | 5/1985 | Delony et al. | 204/299 R |
| 4,574,040 | 3/1986 | Delony et al. | 204/299 R |
| 4,594,064 | 6/1986 | Anderson | 425/145 |
| 4,762,743 | 8/1988 | von Alven et al. | 428/156 |
| 4,773,984 | 9/1988 | Flesher et al. | 204/299 R |
| 4,784,738 | 11/1988 | Sleeter et al. | 204/182.8 |
| 4,874,490 | 10/1989 | Hochstrasser | 204/182.1 |
| 5,071,531 | 12/1991 | Soane | 204/182.8 |

OTHER PUBLICATIONS

Anne–Lise Borresen, et al. Constant denaturant gel electrophoresis as a rapid screening technique for p53 mutations. Proc. Natl. Acad. Sci. USA. vol. 88, pp. 8405–8409, Oct. 1991 Medical Sciences.

Birgitte Smith–Sorensen, et al. Screening for mutations in human HPRT cDNA using the polymerase chain reaction (PCR) in combination with constant denaturant gel electrophoresis (CDGE). Mutation Research, 269 (1992) 41–53. 1992 Elsevier Science Publishers B.V.

Eivind Hovig, et al. Constant denaturant gel electrophoresis, a modification of denaturing gradient gel electrophoresis, in mutation detection. Mutation Research, 262 (1991) 63–71.

Primary Examiner—Howard E. Schain
Assistant Examiner—C. Delacroix-Muirheid
Attorney, Agent, or Firm—Townsend and Townsend and Crew LLP

[57] ABSTRACT

Gradient gels are formed in a slab gel enclosure by introducing gel solution through a channel in one of the two or more spacers which set the thickness of the gel. The channel opens into the gel space through an aperture in the inner longitudinal edge of the spacer at approximately mid-length along the edge, and filling of the gel space with the solution is performed with the enclosure rotated onto its side. In certain embodiments of the invention, the opposing spacer contains an aperture as well, plus a channel leading from the aperture to the exterior of the enclosure, for venting of air from the gel space as the space is being filled with the gel-forming liquid.

6 Claims, 3 Drawing Sheets

ELECTROPHORESIS SLAB GEL ENCLOSURE FOR GRADIENT GELS

This invention relates to electrophoresis in slab-shaped gels, and in particular to gradient gels and their preparation.

BACKGROUND OF THE INVENTION

Nucleic acid sequencing and analysis, as well as other types of macromolecular separations, are often performed by electrophoresis in slab gels. Many of these procedures use gradient gels as a means of increasing sensitivity, range and versatility.

Polyacrylamide gels with a gradient in porosity are prepared by varying the concentration of acrylamide in one direction along the gel. The variation permits the gel to be used for fractionating a mixture of species with molecular weights spanning a broad range. Depending on the suspected composition of the mixture, the gradient can be linear, exponential, or specifically tailored to conform to any selected profile. Separations can be performed with the gradient either parallel or perpendicular to the direction of electrophoretic migration, although most of these separations are performed with a parallel gradient.

Gels containing a denaturant are used in certain separations of nucleic acids, particularly DNA sequencing procedures. A gradient of the denaturant is often used as a means of differentiating among sequences to distinguish fragments of mutant genes from those of wild-type genes. The partial melting, or strand dissociation, of a double-stranded DNA fragment due to exposure to denaturing conditions is sequence-dependent, with certain domains of the double strand dissociating (and thus forming single-strand loops) more readily than others. These discrete melting domains within the fragment cause a retardation in the electrophoretic mobility of the fragment as a whole. The retardation is therefore related in a complex way to the base sequence of the fragment. By applying the DNA, whether mutant or wild type, in a continuous line across one edge of the slab gel and using a denaturing gradient perpendicular to the direction of migration, each fragment will form an S-shaped curve, indicating a drop from a relatively fast migration rate to a relatively slow rate at the denaturant concentration at which the least stable domain of the fragment melts. The inflection points of these curves will be distributed along the gradient, with the S-curves and hence the fragments being readily differentiated on the basis of their base sequences rather than their molecular size.

Gels with denaturing gradients parallel to the direction of migration are also used, notably as the second stage of a two-dimensional separation. Separation along the first dimension is usually a conventional constant gel separation, where the differentiation is on the basis of molecular size. Separation along the second dimension then differentiates on the basis of sequence. Using multiple lanes in the first, constant-gel stage, the lane containing the separated fragments is removed and placed along one edge of the gradient gel at the end of the gradient containing the lowest denaturant concentration. As the fragments migrate into high-denaturant concentrations, they separate into subfragments according to their base sequences.

Depending on the size of the gel and the type of separation being performed, the ease with which a gradient gel can be formed depends on the dimensions of the slab. The slabs are frequently of much greater length than width, and both length and width are several orders of magnitude greater than the depth of the slab. Slabs such as these are generally formed between two glass plates with thin spacer strips along the side edges of the plates, separating the plates by their thickness, and thereby establishing the thickness of the gels held in between. This arrangement makes it difficult in some cases to inject gelforming solution of continuously varying composition in such a manner that the incoming liquid will not mix and thereby obscure the gradient sought to be formed. In addition, for perpendicular gradient gels, the gel must be cast in one direction, then rotated 90° to run the electrophoresis. The present invention addresses these problems by providing a means of injecting gel-forming solution through the spacer strips in such a manner that the solution can be injected into the space with the enclosure rotated on its side so that the spacer strips are essentially horizontal, and the enclosure then rotated back to the upright position to engage the electrophoresis cell for sample preparation.

SUMMARY OF THE INVENTION

The present invention resides in an enclosure in which a gel slab can be both cast and used, and which includes a pair of glass plates and a pair of spacer strips as mentioned above, but which further includes a passageway or channel in at least one of the spacer strips leading to an opening in the edge of the strip facing the gel space. The channel is used for feeding the gel-forming solution into the gel space, which is performed with the gel enclosure rotated approximately 90° so that the spacer is substantially horizontal. The opening may be positioned at any location along the length of the spacer, the selection depending on the direction of the intended gradient as well as on whether the opening is to be used as an inlet for the solution or as a vent. For a gradient in the direction perpendicular to the spacer, the opening may conveniently be placed somewhere within the lower half of the inner edge of the strip. For a gradient parallel to the strip, the opening may be placed at or near one end of the inner edge and the enclosure will not be rotated 90° during filling. Certain embodiments of the invention also include a vent opening in the second spacer strip to allow for the escape of air through that strip while the gel space is being filled. This vent opening will also lead to a channel in the strip, through which the vented air will flow. This vent opening will generally function most effectively if it is located toward one end of the inner edge of the strip in which it is formed, to facilitate the escape of all of the air.

At the other end of the channel in each strip is a further opening. One of these openings provides access to the channel from a source of the gel-forming solution, while the other is either open to the atmosphere or joined to tubing or other type of conduit which is open to the atmosphere, and can be closed after the filling of the channel to seal the channel.

These and other features of the invention and its preferred embodiments will become evident from the description which follows.

DETAILED DESCRIPTION OF THE INVENTION AND PREFERRED EMBODIMENTS

Figure 1:
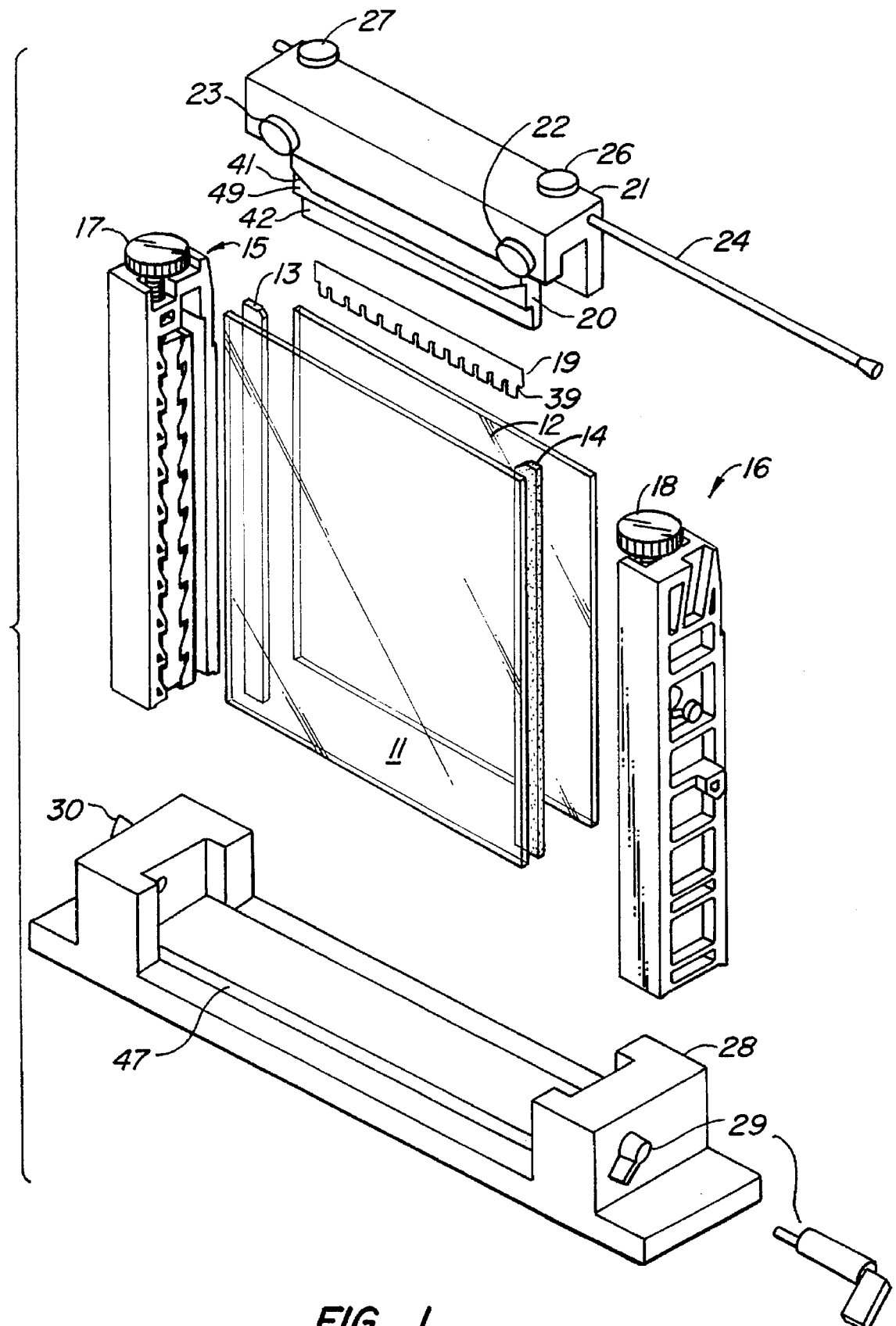
FIG. 1 is an exploded view in perspective of a gel enclosure representing one illustrative embodiment of the present invention.

The slab gels to which this invention is addressed are usually formed in enclosures which leave two opposing edges of the slab (the top and bottom) exposed for electrical contact with the appropriate electrodes through buffer solutions. Thus, the glass plates mentioned above usually form the walls of the enclosure which contact the two broad faces of the gel slab, while the spacer strips contact the side edges of the slab. During casting of the gel, the otherwise open gaps between the plates along the top and bottom edges of the plates are temporarily sealed off. The top gap may be sealed by a "comb" or toothed device which forms wells designed to hold samples at intervals along the top edge of the gel. Alternatively, no sealing device at all may be inserted, or the sealing device may be one with a straight edge, if the sample is to loaded in a continuous line along the top of the gel. The bottom gap is often sealed off by placing the enclosure in a casting stand which supports the enclosure in a stable upright position and compresses a gasket or similar element against its exposed lower edge. One example of such a casting stand is that disclosed by Sleeter, D., et al., in U.S. Pat. No. 4,784,738, issued Nov. 15, 1988. This patent is incorporated herein by reference.

The enclosures themselves, except for the modification introduced by the present invention, may be similar to that shown by Delony, et al., in U.S. Pat. No. 4,518,476, issued May 21, 1985. This patent is also incorporated herein by reference. The enclosure shown in Delony, et al. consists of a pair of glass plates, a pair of thin spacer strips, and a pair of end clamps, one for each lateral edge of the enclosure to hold the two plates together and to compress a spacer strip between the edges of the plates along each side in a fluid-tight manner. As alternatives, the plates may be of materials other than glass, such as polycarbonate or other non-electrically-conducting polymeric material. The plates can also be contoured rather than flat, and having a perimeter shape which is other than square or rectangular. Flat, rectangular glass plates are widely used, however, since glass is inexpensive, electrically a non-conductor, and compatible with the gel material, and the rectangular shape is convenient both in terms of the ease of its manufacture and the use of flat linear spacers, as well as for purposes of performing electrophoresis with linear migration paths, either in a single direction or in successive orthogonal directions. In DNA sequencing studies where a long migration path is needed, glass plates of an elongated rectangular shape are generally required. Spacer strips will then be used which extend the full length of each long edge of the glass plates.

The glass plates depicted by Delony, et al. are of dissimilar length along one dimension such that the top edge of one of the plates is slightly lower than the top edge of the other. This is done so that the excess height of the higher plate serves as one side of the receptacle which holds the upper buffer solution in contact with the upper edge of the gel, which is level with the upper edge of the shorter plate. This arrangement may be used in the present invention as well, but is not required. Plates of identical size and shape may be used as well.

The spacer strips are made of any conventional material which is electrically nonconducting and can be formed into a strip with a thickness of high uniformity and low tolerance. The channel in each strip which provides either for the supply of gel solution or for the venting of air in accordance with the present invention may either extend through the entire thickness of the strip, or only partially through, i.e., as a groove in one of the broad faces of the strip.

The end clamps depicted by Delony, et al., are each adjustable by a manually operated screw to accommodate a range of thicknesses of the combined glass plates and spacer, and to apply pressure to these parts equally along their lengths to seal the liquid inside while minimizing the risk of breakage. Alternative means of securing the plates and spacers may also be used, such as spring-loaded clamps or clamps which contain a resilient gasket-like material such as rubber against which the plates and spacer are force fit, with pressure applied either discontinuously at discrete locations along the length of a glass plate or continuously along the entire length.

Turning now to the drawings, FIG. 1 illustrates a gel enclosure in an exploded perspective view, as one illustration of an implementation of the concepts which form this invention. The enclosure consists of two glass plates 11, 12, two spacers 13, 14 to set the gap width between the glass plates, and two end clamps 15, 16 to hold the plates and spacers together in a sandwich-type arrangement, the clamps operable by manually operated screws 17, 18. The end clamps are similar to those disclosed by Delony, et al., except that these clamps also include ports for feeding gel solution to the interior of the gel enclosure and for venting the interior as the solution is being fed into it.

In this enclosure, the two glass plates are of unequal height, the forward plate 11 having an upper edge that is higher than that of the rear plate 12. The spacers 13, 14 are each of a height equal to that of the taller forward plate 11, thereby extending above the shorter plate. The lower edges of both plates and both spacers are all at the same height.

At the top of the enclosure are three components to shape and seal the top edge of the gel. One of these is a comb-shaped insert 19 which fits in the gap between the glass plates and contains downwardly extending teeth to form sample wells along the top edge of the gel. The other two are a gasket 20 which seals off the upper edge of the gap, and a holder 21 which retains the gasket and clamps the gasket into a sealing position at the top of the glass plates by virtue of a tightening screws 22, 23. The holder also contains a sliding rod 24 passing through the full length of the holder through which the rod can be slid back and forth to extend from either of the two ends of the holder. The rod as shown in the drawing is extended toward the right. The position of the rod is secured by tightening screws 26, 27. When extended, the rod serves as a prop to support the enclosure when the enclosure is tilted on its side for filling with gel solution in a gradientforming manner. The gasket 20 and holder 21 prevent leakage when the enclosure is tilted on its side. At the bottom of the enclosure is a casting stand 28 with a foam pad 47 to which the bottom edge of the enclosure, including the end clamps, is secured by further cams 29, 30.

Figure 2:
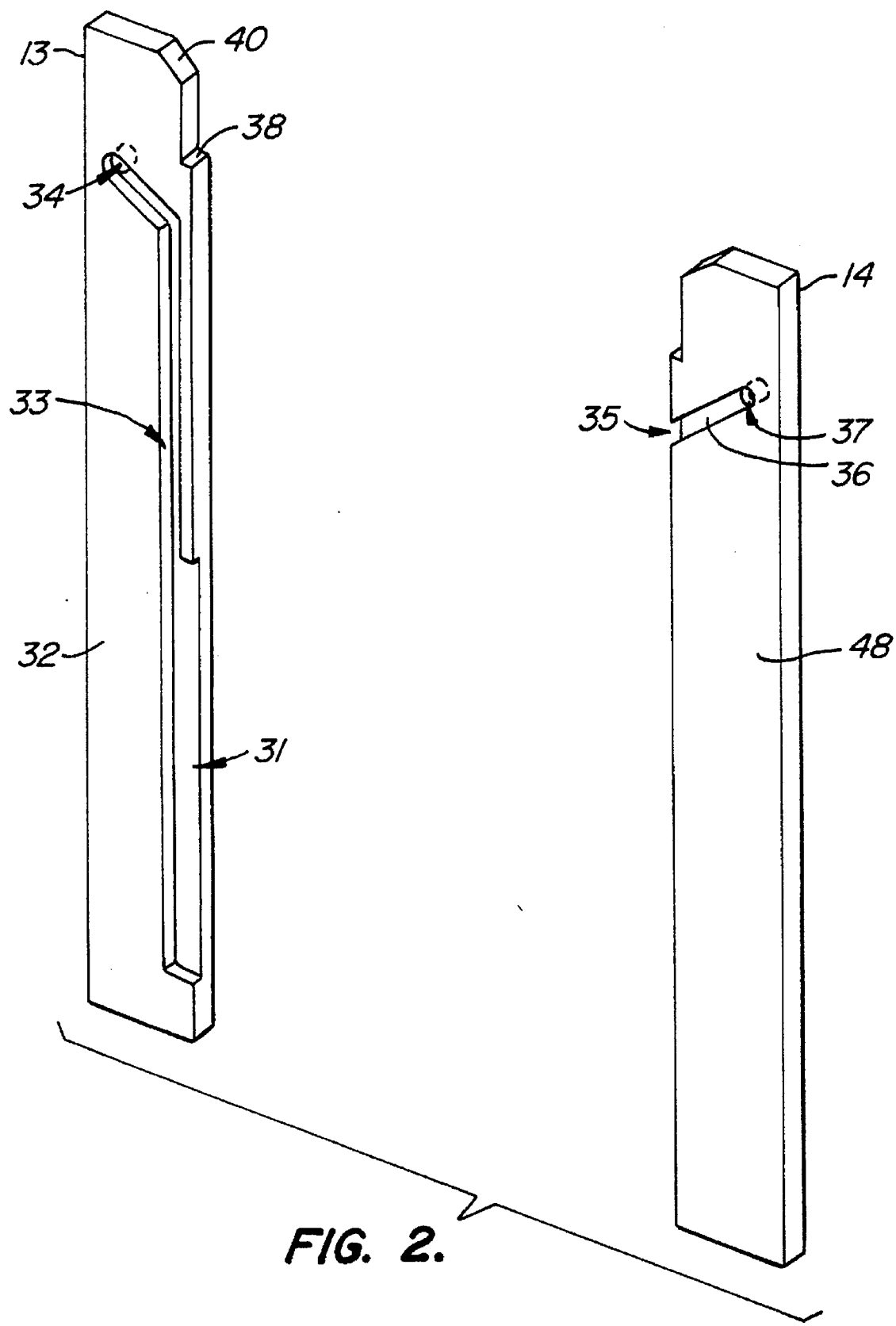
FIG. 2 is a perspective view of the two spacer strips included in the gel enclosure of FIG. 1.

The spacers 13, 14 contain the apertures and channels described above, but these are best seen in FIG. 2, which shows the spacers in the same perspective view as that of FIG. 1 but enlarged. The gel space is located between the spacers.

The spacer 13 on the left in this embodiment is used for supply of the gel solution to the gel space. This spacer contains an elongated aperture 31 in the inner edge of the spacer, opening into the gel space. The depth of the aperture 31 in this case is approximately half the depth of the spacer, extending from one broad face 32 of the spacer to a depth at approximately half of the thickness of the spacer. The aperture is fed by a channel 33 which is in turn supplied by a further aperture 34 through which the gel solution will enter the channel. The channel is actually a groove cut into the spacer along the broad face 32 of the spacer.

The spacer 14 on the right is used for venting air from the gel space. An aperture 35 on the inner edge of the spacer opens into the gel space as does the aperture 31 on the left spacer 13. Likewise, a channel 36 leads from this aperture to a further aperture 37 near the upper end of the spacer. The channel 36 is open at one broad face 48 of the spacer and extends to a depth which is approximately half the thickness of the spacer, in the same manner as the channel 33 on the left spacer. The apertures 34, 37 at the upper ends of both spacers are holes extending all the way through each spacer.

The upper inner corners of each of the spacers are specially shaped to hold the comb-shaped insert 19 and the gasket 20 (FIG. 1) in place. The comb-shaped insert rests on a shoulder or step 38 (FIG. 2), the two shoulders mating with corresponding inverted shoulders 39 at each end of the comb-shaped insert 19 (FIG. 1). The gasket 20 rests on a beveled or angled corner 40 (FIG. 2) on each spacer, the two angled corners mating with similarly angled corners 41 on the gasket. The forward face of the gasket is formed into three wide steps, the middle step 49 contacting the upper exposed regions of the broad faces of the spacers, and the lower step 42 contacting the broad face of the lower glass plate.

Figure 3:
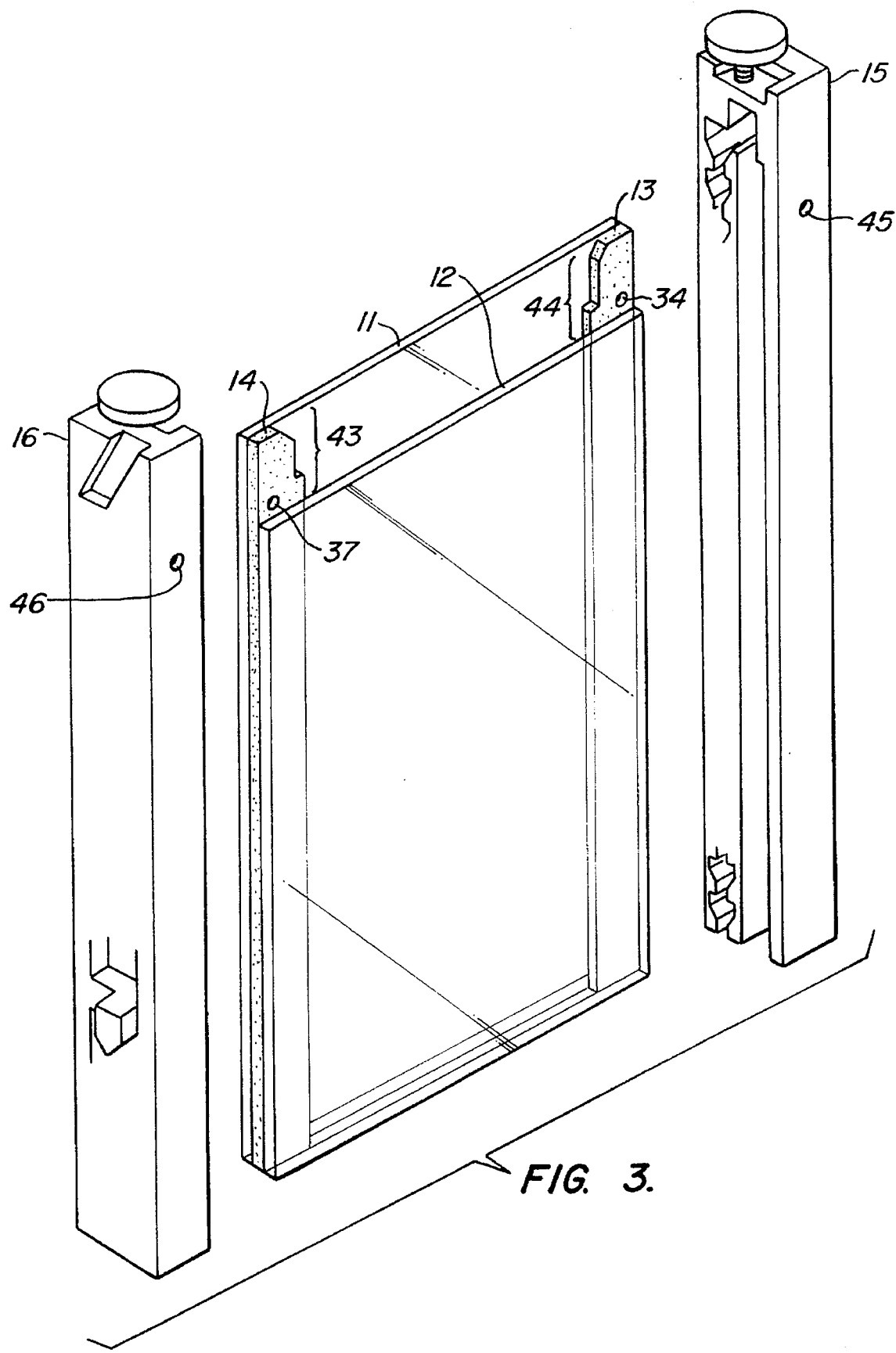
FIG. 3 is a partially exploded view in perspective of the rear side of the gel enclosure of FIG. 1.

Turning next to FIG. 3, the reverse side of the enclosure is shown, with the glass plates and spacers placed against each other and the vertical proportions exaggerated to emphasize the differences in height. Each spacer has an upper segment 43, 44 which extends above the upper edge of the shorter glass plate, and the apertures 34, 37 are in these segments. Apertures 45, 46 in the end clamps are in alignment with the apertures 34, 37 in the spacers when the clamps are positioned over the plates and spacers. The aligned apertures provide access to the exterior. One of these apertures 45 will be connected to tubing through a fitting and an O-ring seal, the tubing supplying gel-forming solution. The other aperture will be left open for venting air.

To load the gel space with gel-forming solution while forming a gradient in a direction perpendicular to the spacers, the parts shown in FIG. 1 are assembled so that the gel space is fully enclosed in a fluid-tight manner except for the apertures and channels in the spacers. Supply tubing is then secured to the aperture 45 in the end clamp at the side which contains the spacer 13 with the channel opening at the center of the inner edge of the strip. The tubing is then connected to a gradient forming apparatus. Any of the variety of devices currently known, such as the conventional gravitational gradient mixer in common use, may be used.

Before the solution is introduced into the gel space, the entire enclosure, sealed on all sides, is rotated through an angle slightly less than 90°, so that the spacer through which the solution will enter the gel space is at the bottom and the vent aperture is at the top. With an angle slightly less than 90°, the upper spacer will slope upwards toward the vent aperture, to assure that no air is entrapped in the gel space as it is being filled. Once the space is filled, the enclosure is rotated further to the full 90° angle so that the spacers are perpendicular to the gravity vector, and the gel is permitted to form.

Many variations on the construction and configuration shown in these drawings which still embody the basic concepts of the invention will be readily apparent to those skilled in the art. For example, a pair of gels can be formed side-by-side between the same two glass plates, separated by a central spacer of the same thickness as the spacers at each of the two side edges. The central spacer may be a symmetrical version of the right spacer 14 shown in FIG. 2, with two independent vent channels and two independent vent holes, one channel and hole leading to each of the two long side edges of the spacer. Both upper corners of the spacer will contain angled surfaces and steps symmetrically arranged. The end spacers will be mirror images of each other, one of which will be identical to the left spacer 13 shown in FIG. 2. As an alternative to the symmetrically apertured central spacer, the vent holes may be in the gasket. As for the gasket itself and the comb-shaped insert, individual gaskets and inserts may be used for each of the two gel spaces, or a single gasket and comb-shaped insert extending across the combined width of both gels may be used. Gradient gels may be formed in each of the two spaces by filling each space individually and allowing the gel in the first space to solidify before the other space is filled. The first space is filled and the gel solidified therein with the enclosure tilted to one side; the enclosure is then rotated 180° to fill the second space and solidify the gel therein. In the single-gel embodiments as well, the vent passage on the spacer may be eliminated entirely by the use of a shorter spacer on the vent side or by any arrangement or configuration of the parts which leaves a gap at the top of the spacer. As a still further alternative, the holes 34 and 37 in the spacers may be replaced by openings in the upper edges of the spacers rather than in their broad faces as shown, with the channelis leading appropriately to these openings, and corresponding aligned passages in the gasket or end clamps.

The end clamps and the means of sealing the upper and lower edges of the gap between the glass plates can also be varied, in addition to the variations mentioned above. The end clamps may range from the relatively complex structures disclosed by Delony, et al., U.S. Pat. No. 4,518,476, to structures as simple as conventional binder clips (metallic spring-loaded clips normally used for holding together sheets of paper), with two or more such clips along each side edge of the glass plate sandwich, or structures with other screw-tightened or cam-tightened clamping parts, with the screws or cams pointing in any of various directions. Alternatives to the gasket shown in the drawings for the upper edge of the glass plate sandwich might include gaskets which extend into the space between the glass plates, gaskets which remain entirely above the upper edges of the glass plates as opposed to extending a short distance along the broad face of one of the glass plates as does the gasket in the drawings, and gaskets which are compressed from above (i.e., along a direction parallel to the glass plates) rather than from the front or back as shown in the drawings. Alternatives to the casting stand which seals the lower edges of the gap between the glass plates are removable adhesive materials, and gaskets compressed against the plates, either from the front or back or into the edge itself along a direction parallel to the glass plates, and any of a variety of other configurations.

In general, it will be readily apparent to those skilled in the art that still further variations may be made in the shapes and configurations, operating methods and other parameters of the system described herein without departing from the spirit and scope of the invention. Accordingly, the foregoing is offered primarily for purposes of illustration.

What is claimed is:

1. An enclosure for a slab gel for electrophoretic separations, comprising:

first and second plates, each with four edges defined as two opposing side edges, a top edge and a bottom edge;

first and second spacer strips for placement between said plates to define an open space for said slab gel;

a first aperture in a longitudinal edge of said first spacer strip at a location displaced from either end thereof, a second aperture in said first spacer strip at a location other than said longitudinal edge and closer to one end of said first spacer strip, means for communicating said second aperture with a supply of gel-forming liquid, and a channel in said first spacer strip communicating said first aperture with said second aperture; and clamping means for clamping said first and second plates together with said first and second spacer strips in between.

2. An enclosure in accordance with claim 1 further comprising a third aperture in a longitudinal edge of said second spacer strip, a fourth aperture in said second spacer strip at a location other than said longitudinal edge, and a channel in said second spacer communicating said first aperture with said second aperture.

3. An enclosure in accordance with claim 1 in which said first spacer strip is defined by a pair of opposing faces and a perimeter edge, said first aperture is in said perimeter edge, and said second aperture is in one of said opposing faces.

4. An enclosure in accordance with claim 1 in which the majority of said first aperture is located in said longitudinal edge of said first spacer strip in the half length thereof opposite the half length in which said second aperture is located.

5. An enclosure in accordance with claim 1 in which said clamping means contains a through passage to permit access to said second aperture.

6. An enclosure in accordance with claim 1 further comprising:

upper sealing means for sealing said open space along said top edges of said first and second plates; and lower sealing means for sealing said open space along said bottom edges of said first and second plates.

* * * * *